US006180397B1

United States Patent
Binder

(10) Patent No.: US 6,180,397 B1
(45) Date of Patent: Jan. 30, 2001

(54) INCUBATOR WITH EXTERNAL GAS FEED

(76) Inventor: Peter Michael Binder, Am Herrenholz 5, D-78359 Nenzingen (DE)

(*) Notice: Under 35 U.S.C. 154(b), the term of this patent shall be extended for 0 days.

(21) Appl. No.: 09/285,131

(22) Filed: Apr. 2, 1999

(30) Foreign Application Priority Data

Apr. 7, 1998 (DE) .............................................. 198 15 548

(51) Int. Cl.[7] .................................................. C12M 3/00
(52) U.S. Cl. .................................... 435/303.1; 435/286.6; 435/809; 422/104
(58) Field of Search ........................ 435/3, 286.6, 303.1, 435/809; 422/104; 600/21, 22; 119/311, 315–317

(56) References Cited

U.S. PATENT DOCUMENTS

| 4,689,303 | 8/1987 | Kraft et al. . |
| 5,418,131 | * 5/1995 | Butts . |
| 5,800,335 | * 9/1998 | Koch et al. . |

FOREIGN PATENT DOCUMENTS

| 117 329 | * 1/1976 | (DD) . |
| 0 131 541 | 5/1984 | (EP) . |
| 60-110284 | 6/1985 | (JP) . |
| 6-245753 | 9/1994 | (JP) . |

* cited by examiner

Primary Examiner—William H. Beisner
(74) Attorney, Agent, or Firm—Foley, Hoag & Eliot LLP

(57) ABSTRACT

An incubator with an external gas feed is disclosed, wherein a gas is supplied to an interior space of the incubator to maintain an interior atmosphere with a constant gas-to-air ratio. The gas is supplied to the interior space through a gas nozzle forming a gas jet. The gas jet draws in the interior atmosphere through an injector effect, thereby thoroughly mixing the gas with the interior atmosphere.

10 Claims, 2 Drawing Sheets

INCUBATOR WITH EXTERNAL GAS FEED

BACKGROUND OF THE INVENTION

1. Field of the Invention

This application relates to the field of incubators and more particularly to the field of incubators having an external gas feed.

2. Description of Related Art

Incubators are used to cultivate cell cultures. It is desirable to maintain inside the incubator which receives the cell cultures, conditions which are most advantageous for providing optimum cell growth. Particularly important is a constant temperature and a high relative humidity.

Typically, incubators with an external gas feed also maintain in the interior space of the incubator an interior atmosphere with a constant mixing ratio between air and the added gas, which is typically $CO_2.O_2$ or $N_2$ may also be added if desired. In order to compensate for disturbances that occur when the incubator with the external gas feed is opened, the gas concentration in the interior space is measured and the gas supply is regulated to maintain a constant gas-to-air mixing ratio.

Conventional incubators with an external gas feed typically include a fan to thoroughly and uniformly mix the added gas with the interior atmosphere. The fan can be implemented in form of a miniature fan, with the drive motor of the fan also arranged in the interior space. Alternatively, only the fan wheel can be placed within the interior space, while the drive motor is located outside the incubator housing. The fan with the drive represents a relatively complex and expensive component. The moving parts of the fan located in the interior space are typically heavy and are also difficult to clean and sterilize, so that the fan itself can pose a contamination risk. If the drive motor is located outside the interior space, then the drive shaft for the fan wheel has to penetrate the wall of the inner vessel of the incubator, which requires an opening and therefore also increases the contamination risk. Moreover, a fan tends to whirl the airborne germs that exist in the interior space, around and spread these germs over the cell cultures.

It is desirable to provide an incubator with an external gas feed that is less complicated and less expensive to build and that also reduces the contamination risk.

SUMMARY OF THE INVENTION

In general, according to one aspect of the invention, the gas is introduced into the interior space in form of a gas jet, wherein the injector effect of the gas jet is advantageously employed to mix the gas with the interior atmosphere. The gas injected through the gas nozzle entrains the air/gas mixture of the surrounding interior atmosphere, so that the injected gas is rapidly and thorough mixed with the interior atmosphere.

The injector effect may be improved by incorporating in the gas nozzle a jet tube, wherein the gas jet of the jet tube flows coaxially into a mixing tube. The injector effect of the gas jet creates in the annular space between the jet pipe and the mixing tube a reduced pressure which enhances the suction with which the surrounding interior atmosphere is drawn in and produces an improved mixing effect.

The gas nozzle is a simple component and may be made of stainless steel. The gas nozzle can be manufactured cost-effectively and does not require an external drive or a supply of energy. Due to the simple design and the choice of material for the gas nozzle, and more particularly due to the fact that the gas nozzle does not include moveable mechanical parts, the gas nozzle can be easily and thoroughly cleaned and sterilized.

During operation of the incubator with an external gas feed, only small quantities of gas have to be added to compensate for gas losses. The flow cross-section of the gas nozzle can therefore be kept small, which is advantageous for producing the required flow momentum of the gas jet. The small flow cross-section has the additional advantage of restricting the overall gas flow exiting the nozzle. In the event of, for example, a malfunction of the regulator which could allow gas to flow out of the gas nozzle unintentionally over a longer period of time, the total amount of gas that leaves the gas nozzle is still relatively small as a result of the small flow cross-section of the nozzle. This feature largely eliminates interruptions in a laboratory operation or injuries to the persons working in the laboratory.

The gas nozzle is preferably arranged on the top surface of the interior space of the incubator. With this arrangement, the gas jet is not obstructed in its downward motion inside the interior space and can therefore unimpededly draw in the interior atmosphere from all sides to optimally mix the gases. Typically, the supplied gas is $CO_2$ which is heavier than air. Consequently, the $CO_2$ gas entering the interior space moves downwardly also due to its higher specific gravity, thereby extending the path of the gas to attain a complete mixing with the interior atmosphere.

The concentration of the supplied gas is typically determined with a gas sensor located in the interior space. The measured concentration is used to regulate and control the mixing ratio of the interior atmosphere. The gas jet is preferably injected in close proximity to the gas sensor, allowing the gas sensor to respond quickly and thereby reducing the inertia of the control system.

Further features and advantages of the present invention will be apparent from the following description of preferred embodiments and from the claims.

DETAILED DESCRIPTION OF PREFERRED EMBODIMENT(S)

Figure 1:
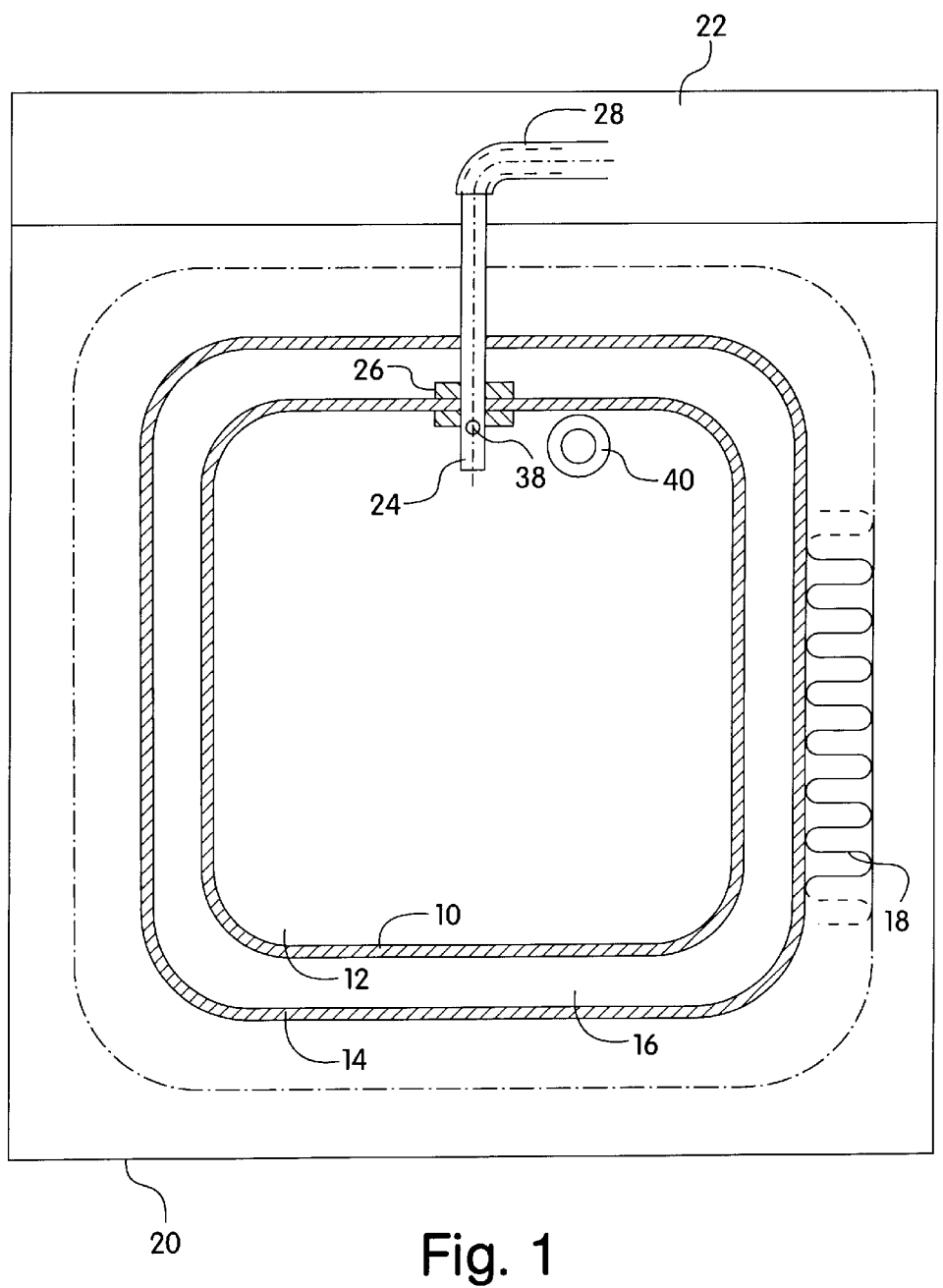
FIG. 1 is a vertical cross section through an incubator with an external gas feed according to the invention.
Figure 2E:
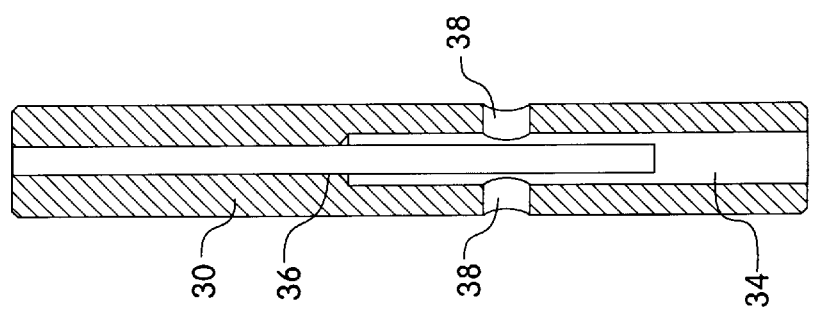
FIG. 2e is an axial cross section through the assembled gas nozzle.
Figure 2D:
FIG. 2d is a jet pipe.
Figure 2B:
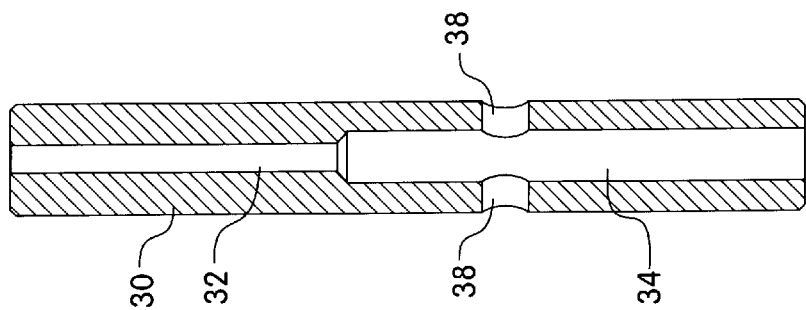
FIG. 2b is an axial cross section of the nozzle jacket.
Figure 2C:
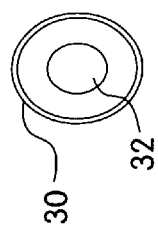
FIG. 2c is an axial front view of an outer end of the nozzle jacket.
Figure 2A:
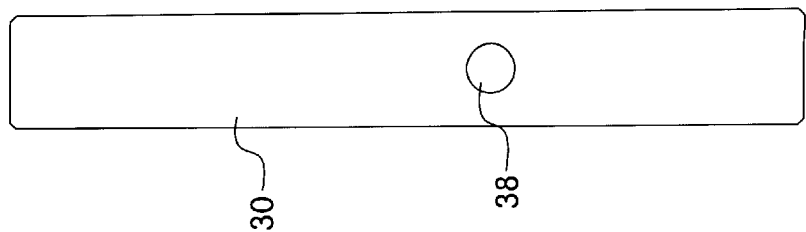
FIG. 2a is a side view of a gas nozzle.

FIG. 1 shows schematically a vertical cross section through an incubator with an external gas feed, in particular an incubator having a $CO_2$ feed. The incubator includes an inner vessel 10 which is preferably deep drawn or welded from stainless steel or copper sheet. The inner vessel 10 encloses an interior space 12 adapted to receive the cell cultures (not shown). The inner vessel 10 is surrounded by an outer vessel 14, with an air jacket 16 formed between the inner vessel 10 and the outer vessel 14. The air enclosed in the air jacket 16 can be heated to maintain an interior atmosphere in the interior space 12 at a predetermined temperature. A thermal insulation 18 is applied to the outside of the outer vessel 14. The incubator and the external gas feed is enclosed in a housing 20. A control box 22 is located on top of the housing 20, wherein the control box 22 may include a power feed, control devices and the like, which are not shown in detail. The open front face of the inner vessel 10 can be closed with a door (not shown).

A gas nozzle 24 is located towards the rear near the center of the top surface of the inner vessel 10. Details of the gas nozzle 24 are illustrated in FIGS. 2a–2e. The gas nozzle 24 penetrates the inner vessel 10 and the outer vessel 14 and is secured to the vessels 10, 14 with a bulkhead fitting 26. The gas nozzle 24 extends upwardly from the housing 20 into the control box 22. Inside the control box 22, the gas nozzle 24 is connected to a gas source, for example a gas tank (not shown), through a hose 28 and a regulator (not shown). The supplied gas is typically $CO_2$. If the partial pressure of $O_2$ and/or $N_2$ have to be controlled, then $O_2$ and/or $N_2$ can also be supplied.

As seen in FIGS. 2a–2e, the gas nozzle 24 includes a cylindrical nozzle jacket 30 made of stainless steel or another material that can be sterilized with hot air at temperatures reaching 180° C. The nozzle jacket 30 is provided with a coaxial through bore 32. In the axial section of the nozzle jacket 30 located outside the inner vessel 10, the bore has the form of a guide bore 32 having a relatively small diameter (for example, 2 mm). In the axial region of the nozzle jacket 30 located inside the inner vessel 10, the bore widens to from a mixing tube 34 with a larger inside diameter than that of the guide bore 32 (for example, 4 mm). A jet pipe 36 which is also made of stainless steel or of another material that can be sterilized using hot air, has an outside diameter which matches the inside diameter of the guide bore 32. An inner bore with a smaller cross-section, for example, with a diameter of 1 mm, extends completely through the jet pipe 36 in the longitudinal direction of the jet pipe 36. The jet pipe 36 is inserted into the guide bore 32 so as to form a seal with the guide bore 32. The length of the jet pipe 36 is selected so that an outer end of the jet pipe 36 is flush with the outer end of the nozzle jacket 30 that extends into the control box 22, and that an inner end of the jet pipe 36 opposite the outer end terminates axially in a center region of the mixing tube 34, as illustrated in detail in FIG. 2e. For example, the mixing tube 34 may have an axial length of approximately 30 mm, with the jet pipe 36 taking up approximately two-thirds of the axial length of the mixing tube 34. An annular space is formed between the inner wall of the mixing tube 34 and the outer wall of the jet pipe 36. Intake openings 38, which penetrate the wall of the nozzle jacket 30 in the region of the mixing tube 34, terminate in the annular space. The illustrated embodiment shows two diametrically opposed intake openings 38 that are located in the interior space 12.

A gas, preferably $CO_2$, is blown into the interior space 12 through the jet pipe 36. The gas jet exiting from the jet pipe 36 produces a region of reduced pressure due to the injector effect in the mixing tube 34. The reduced pressure causes the air-gas mixture of the interior atmosphere in the interior space 12 to be drawn into the mixing tube 34 through the intake openings 38. The interior atmosphere drawn into the intake openings 38 mixes with the gas exiting the jet pipe 36 in the end section of the mixing tube 34 that is located downstream of the outlet end of the jet pipe 36. Consequently, the supplied gas is already well mixed with the interior atmosphere when the gas exits from the mixing tube 34 into the interior space 12.

A gas sensor 40, for example, a $CO_2$ sensor, is arranged near the top on the rear wall of the inner vessel 10. The gas sensor 40 measures an actual value of the gas concentration, for example the $CO_2$ concentration, of the interior atmosphere and controls the regulator (not shown) to adjust the flow of the gas through the gas nozzle 24.

While the invention has been disclosed in connection with the preferred embodiments shown and described in detail, various modifications and improvements thereon will become readily apparent to those skilled in the art. For example, the gas nozzle may be used to mix a supplied gas with a surrounding atmosphere in other open or enclosed spaces, such as storage areas that may not be heated. Accordingly, the spirit and scope of the present invention is to be limited only by the following claims.

We claim:

What is claimed is:

1. Incubator for cell cultures with a gas supply, comprising:

a housing having an inner vessel enclosing an interior space which receives the cell cultures and has an interior atmosphere; and a gas nozzle penetrating the inner vessel and extending into the interior space and supplying a gas to the interior space, the gas nozzle producing a gas jet which exits into the interior space, wherein the gas jet draws in the interior atmosphere and mixes the gas with the interior atmosphere so as to maintain a concentration of the interior atmosphere with a predetermined gas-to-air ratio.

2. Incubator with a gas supply, comprising:

a housing enclosing an interior space having an interior atmosphere; and a gas nozzle extending into the interior space and producing a gas jet supplying a gas to the interior space, the gas nozzle comprising:

a jacket tube having a first section with a first axial bore having a first diameter and a second section abutting said first section, the second section having a second axial bore with a second diameter that is larger than the first diameter, the second section forming a mixing tube, said first bore continuous with said second bore;

at least one intake opening arranged in a sidewall of the mixing tube; and a jet pipe inserted in the first axial bore and coaxially extending into the mixing tube, with the jet pipe and the mixing tube defining an annular space, wherein at least one of the intake openings terminates in the annular space, wherein the gas jet draws in the interior atmosphere and mixes the gas with the interior atmosphere so as to maintain a concentration of the interior atmosphere with a predetermined gas-to-air ratio.

3. The incubator according to claim 2, wherein the mixing tube—in the direction of the flow—extends past the end of the jet pipe that extends into mixing space.

4. The incubator according to claim 2, wherein at least one of the gas nozzle, the nozzle jacket and the jet pipe are made of a material that can be sterilized using hot air.

5. The incubator according to claim 4, wherein the hot air has a temperature less than or equal to 180° C.

6. The incubator according to claim 4, wherein the material of at least one of the gas nozzle, the nozzle jacket and the jet pipe is stainless steel.

7. The incubator according to claim 2, wherein the gas nozzle is located on an upper surface of the housing.

8. The incubator according to claim 7, wherein the gas nozzle is located near a center on the upper surface of the housing.

9. The incubator according to claim 2, further comprising at least one gas sensor disposed in the interior space, wherein the gas nozzle injects the gas jet proximate to the at least one gas sensor.

10. The incubator according to claim 2, wherein the gas nozzle is sealingly secured to a face of the housing with a bulkhead fitting.

* * * * *